(12) United States Patent
MacGillivray

(10) Patent No.: US 9,669,115 B2
(45) Date of Patent: Jun. 6, 2017

(54) CO-CRYSTALS AND SALTS OF CONTRAST AGENTS AND IMAGING

(71) Applicant: UNIVERSITY OF IOWA RESEARCH FOUNDATION, Iowa City, IA (US)

(72) Inventor: Leonard R. MacGillivray, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 200 days.

(21) Appl. No.: 13/931,603

(22) Filed: Jun. 28, 2013

(65) Prior Publication Data

US 2014/0004051 A1    Jan. 2, 2014

Related U.S. Application Data

(60) Provisional application No. 61/666,078, filed on Jun. 29, 2012.

(51) Int. Cl.
*A61K 49/04* (2006.01)
*A61K 49/00* (2006.01)
*A61K 31/395* (2006.01)

(52) U.S. Cl.
CPC .......... *A61K 49/04* (2013.01); *A61K 49/0047* (2013.01); *A61K 49/0438* (2013.01); *A61K 31/395* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,992,478 A | 2/1991 | Geria | |
| 7,927,613 B2* | 4/2011 | Almarsson et al. | 424/400 |
| 2003/0152519 A1* | 8/2003 | Koenig et al. | 424/9.41 |
| 2011/0223203 A1* | 9/2011 | Berkland | A61K 9/0075 424/400 |
| 2012/0128740 A1* | 5/2012 | Filipcsei | A61K 9/14 424/400 |

OTHER PUBLICATIONS

Wikipedia Iopydol 2015.*
Sekhon (ARS Pharmaceutica 2009, 50, 99-117).*
Wikipedia Diatrizoic acid 2015.*
Benedict, "Stereotactic body radiation therapy: The report of AAPM Task Group 101", Med. Phys. 37 (8), 4078-4101 (2010).
Bucar et al., "Preparation and Reactivity of Nanocrystalline Cocrystals Formed via Sonocrystallization", Journal of the American Chemical Society, 129, 32-33 (2007).
Dekrafft, "Iodinated Nanoscale Coordination Polymers as Potential Contrast Agents for Computed Tomography", Angew. Chem. Int. Ed. Engl., 48, 9901-9904 (2009).
De Vries et al., "Block-Copolymer-Stabilized Iodinated Emulsions for Use as CT Contrast Agents", Biomater. 31, 6537-6544 (2010).
Hahn et al., "Nanoparticles as Contrast Agents for in-vivo Bioimaging: Current Status and Future Perspectives", Anal Bioanal. Chem., 399, 3-27 (2011).
Kong et al., "Nanoparticulate carrier containing water-insoluble iodinated oil as a multifunctional contrast agent for computed tomography imaging", Biomater. 28, 5555-5561 (2007).
Martin, "Synthesis and N.M.R. Spectra of Substituted Aminoiodoacridines", Aust. J. Chem., 32(12), 2637-2646 (1979).
McIntire et al, "Pulmonary Delivery of Nanoparticles of Insoluble, Iodinated CT X-ray Contrast Agents to Lung Draining Lymph Nodes in Dogs", J. Pharm. Sci. 87, 1466-1470 (1998).
McWhinnie et al., "Mono- and Bimetallic Bipyridyl Polyene Complexes Containing 17-Electron Molybdenum Mononitrosyl Centers: Electrochemical, Spectroscopic, and Magnetic Studies", Inrg. Chem. 35(3), 760-774 (1996).
Sander et al, "Pharmaceutical Nono-Cocrystals: Sonochemical Synthesis by Solvent Selection and Use of a Surfactant", Angew. Chem. Int. Ed. 49, 7284-7288 (2010).
Sander, "Expansions of supramolecular chemistry: nanocrystals, pharmaceutical cocrystals, imaging, and decorated olefins", Ph.D. dissertation, University of Iowa, 223 pages 2012.
Whitesides et al., "Molecular Self-Assembly and Nanochemistry: A Chemical Strategy for the Synthesis of Nanostructures", Science 254, 1312-1319 (1991).

* cited by examiner

Primary Examiner — Michael G Hartley
Assistant Examiner — Melissa Perreira
(74) Attorney, Agent, or Firm — Viksnins Harris & Padys PLLP

(57) ABSTRACT

The invention provides co-crystals and salts of contrast agents as well as methods to use and prepare the co-crystals and salts.

15 Claims, 11 Drawing Sheets

CO-CRYSTALS AND SALTS OF CONTRAST AGENTS AND IMAGING

RELATED APPLICATION

This patent application claims the benefit of priority of U.S. Application Ser. No. 61/666,078 filed Jun. 29, 2012. The content of this provisional application is hereby incorporated herein in its entirety.

BACKGROUND

Computed tomography (CT) is a powerful diagnostic tool based on X-ray attenuation that provides 3D or 4D images with spatial resolutions <1 mm for clinical scanners used for humans and about 15 microns for micro-CT used for small animals. Contrast agents including small-molecule contrast agents are frequently injected into patients undergoing CT scans. The contrast agents improve the visualization of structures such as blood vessels and tumors. However, certain properties of current small-molecule contrast agents are not optimal including non-specific distribution of the contrast agent, rapid clearance of the agent by the kidney and toxicity of the agent. In addition, it is difficult to administer certain contrast agents in higher concentrations which would be useful to improve visualization.

Contrast agents of nanometer-scale dimensions are emerging as powerful probes for in vivo imaging in medical and biological diagnostics (Hahn, M. A., et al., Nanoparticles as Contrast Agents for in-vivo Bioimaging: Current Status and Future Perspectives. *Anal Bioanal. Chem.* 2011, 399, 3-27). Iodinated organic molecules are the most universally accepted CT contrast agents used clinically. The high atomic number (Z) element in these agents (i.e., iodine) is typically covalently bound, which makes the agents relatively safe for use in humans. Methods to fabricate nano-scale contrast agents (NCAs) of iodinated molecules have focused on incorporating the molecules into nanoparticles using emulsions, liposomes, lipoproteins, and polymers. The methods have been applied in vivo with varying degrees of success. A common drawback of these iodinated NCAs is that it is often necessary to covalently modify a small-molecule contrast agent for incorporation into a nanoparticle. For example, the agent DTA was converted to an ester to be included into a suspension with a surfactant (McIntire, G. L.; et al., Pulmonary Delivery of Nanoparticles of Insoluble, Iodinated CT X-ray Contrast Agents to Lung Draining Lymph Nodes in Dogs. *J. Pharm. Sci.* 1998, 87, 1466-1470). Iodinated functional groups also often need to be covalently integrated into the backbone of a polymer (de Vries, A.; et al., H. Block-Copolymer-Stabilized Iodinated Emulsions for Use as CT Contrast Agents. *Biomater.* 2010, 31, 6537-6544). In cases where a covalent modification is not required (e.g., liposome), it can be difficult to achieve a high payload of the contrast agent (Konga, W. H.; et al., *Biomater.* 2007, 28, 5555-5561). Moreover, in addition to being time consuming and potentially low-yielding, the covalent approach, de facto, affords a molecule that consists of new covalent linkages (Whitesides, G. M.; et al., Molecular Self-Assembly and Nanochemistry: A Chemical Strategy for the Synthesis of Nanostructures. *Science* 1991, 254, 1312-1319), which can create difficulties when attempting to have the material approved for commercial use and application. Accordingly, there is a need for new compositions (e.g., co-crystals and salts) of contrast agents.

SUMMARY OF THE INVENTION

The invention provides co-crystals and salts of contrast agents associated with co-crystal formers (CCFs).

One embodiment provides a co-crystal comprising:
a) a contrast agent; and
b) a co-crystal former.

One embodiment provides a co-crystal or salt comprising:
a) a contrast agent; and
b) a co-crystal former comprising one or more N-aryl groups.

One embodiment provides a pharmaceutical composition comprising a co-crystal or salt of the invention as described herein, and a pharmaceutically acceptable carrier.

One embodiment provides a method to image a certain part of an mammal (e.g., a human) comprising administering a co-crystal or salt of the invention as described herein to the mammal and imaging the mammal.

One embodiment provides the use of a co-crystal or salt of the invention as described herein as an imaging agent (e.g., a computed tomography imaging agent).

One embodiment provides a method for preparing a co-crystal or salt of the invention as described herein comprising contacting a contrast agent with a co-crystal former.

The co-crystals and salts of the invention may have one or more of the following beneficial properties such as improved solubility, enhanced distribution, decreased toxicity, lower clearance or higher loading of the contrast agent upon administration.

BRIEF DESCRIPTION OF THE FIGURES

FIG. 7A shows the three-component assemblies viewed along the b-axis and 7B shows the packing of zig-zag chains viewed along the c-axis.

FIG. 8A shows the four-component assemblies viewed along the c-axis and FIG. 8B shows the layered arrangement of ATA and ACR molecules viewed along the a-axis.

DETAILED DESCRIPTION

Figure 1:
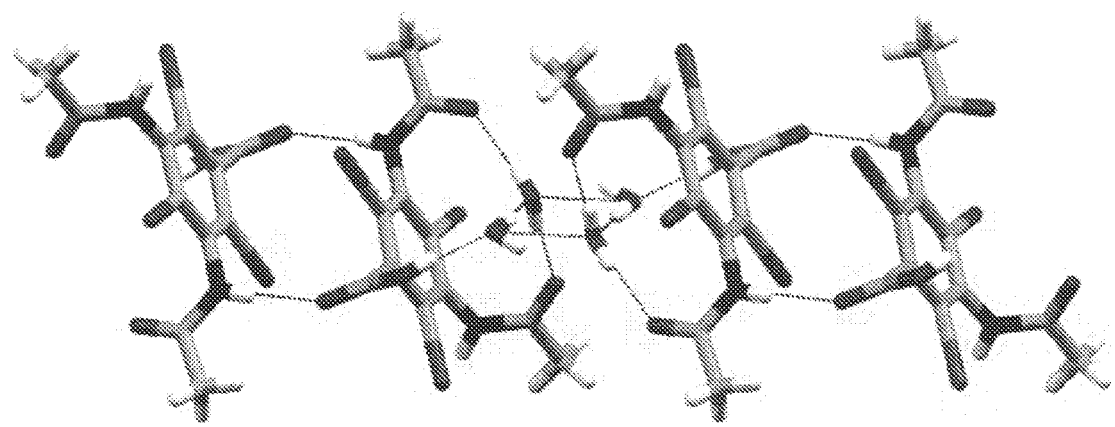
FIG. 1 shows the perspective view of DTA1 wherein DTA molecules assemble into dimers. The dimers propagate along the a-axis to yield 1D columns bridged by water tetramers.

As described herein, certain embodiments of the invention relate to the general concept of combining a contrast agent with a co-crystal former to provide a co-crystal or salt. It has been demonstrated that co-crystals and salts can be readily prepared from available contrast agents and co-crystal formers. The co-crystals or salts can also be prepared on the nanoscale level to provide nanosized cocrystals (e.g., nano-cocrystals) and nanosized salts (e.g., nano-salts).
Co-Crystals and Salts of the Invention.

As used herein the term co-crystal refers to a co-crystal that includes a contrast agent associated with a co-crystal former (CCF) characterized in that there is no discernible transfer of protons between the contrast agent and the co-crystal former. Thus, the contrast agent and CCF of a co-crystal are not charged. One example of this type of co-crystal would be a co-crystal formed between a contrast agent with a carboxylic acid group and co-crystal former with a nitrogen atom wherein the proton of the carboxylic acid is not transferred to the nitrogen of the co-crystal former. This typically occurs when the difference in pKa of the carboxylic acid of the contrast agent and the nitrogen of the CCF is less than or equal to about one. Therefore, co-crystals of contrast agents and CCFs do not include salts of contrast agents and CCFs. Other co-crystals include those wherein the contrast agent has one or more hydrogen bond acceptors or donors and the co-crystal former has one or more hydrogen bond acceptors or donors, wherein there is no discernible transfer of protons between the contrast agent and the co-crystal former.

As used herein the term salt refers to a salt that includes a contrast agent and a co-crystal former (CCF) wherein a proton has been transferred between the contrast agent and the co-crystal former. Thus the contrast agent and the co-crystal former are each charged and therefore are termed herein as salts. One example of this type of salt would be a salt formed between a carboxylic acid group of a contrast agent and a nitrogen of a co-crystal former wherein the proton of the carboxylic acid is transferred to the nitrogen of the co-crystal former. Typically, this type of proton transfer occurs when the difference in pKa of the carboxylic acid and the nitrogen is greater that one. Therefore, salts of contrast agents and CCFs do not include co-crystals of contrast agents and CCFs. Other salts include those wherein the contrast agent has one or more hydrogen bond acceptors or donors and the co-crystal former has one or more hydrogen bond acceptors or donors, wherein at least one proton has been transferred between the contrast agent and the co-crystal former.

The differences between co-crystals and salts of the invention can be readily determined using various techniques such as single-crystal X-ray diffraction, neutron diffraction, infrared spectroscopy, NMR spectroscopy (e.g., solid-state NMR spectroscopy) and combinations of these techniques. The formation of a co-crystal will defined by a lack of a hydrogen atom being transferred between the components of the co-crystal (between the contrast agent and the co-crystal former), as defined by methods used to measure and discern proton transfer including but not limited to X-ray crystallography, neutron diffraction, infrared spectroscopy, and solid-state NMR. For example, when the co-crystal involves a carboxylic acid group, the distances of the two carbon oxygen bonds for the carboxylic acid will be consistent with the presence of a C—O single bond (about 1.43 angstroms) and a C=O double bond (about 1.23 angstroms).

In one embodiment each component of the co-crystal (i.e., the contrast agent and the co-crystal former) is by itself a solid at ambient conditions (i.e., room temperature and standard atmospheric pressure).

The co-crystals and salts of the invention generally have properties that are different than the individual components. For example, the CCF can be used to influence properties of the contrast agent. One particular co-crystal of the invention is a nano-cocrystal. Nano-cocrystals may also be referred to as nano-cocrystal contrast agent (NC3A). In one embodiment the nano-cocrystal has a diameter of about 50-800 nm. In one embodiment the nano-cocrystal has a diameter of about 50-500 nm. In one embodiment the nano-cocrystal has a diameter of about 20-950 nm. In one embodiment the nano-cocrystal has a diameter of about 1-800 nm. One particular salt of the invention is a nano-salt. In one embodiment the nano-salt has a diameter of about 50-800 nm. In one embodiment the nano-salt has a diameter of about 50-500 nm. In one embodiment the nano-salt has a diameter of about 20-950 nm. In one embodiment the nano-salt has a diameter of about 1-800 nm. The use of nanoparticle contrast agents has been reviewed (Hahn, M. A., Anal., Bioanal. Chem., 2011, 399-27).

The contrast agent and CCF are typically designed to associate with each other via non-covalent forces. These non-covalent interactions serve to associate the components (contrast agent and CCF) of the co-crystal or salt together. In one embodiment the contrast agent and the CCF interact with each other via hydrogen bonds. In one embodiment the contrast agent and the CCF interact with each other via ionic bonds. Typically, the co-crystals and salts describe herein have inherent modularity. Thus, a wide-variety of CCFs based on different organic groups and a wide variety of contrast agents can used to prepare co-crystals and salts.

Contrast agents, in addition to their association with CCFs can also form salts with an appropriate counterion when sufficiently basic or acidic. Likewise, CCFs in addition to their association with contrast agents can also form salts with an appropriate counterion when sufficiently basic or acidic.

The co-crystals and salts of the invention may be useful for imaging certain organs or tissues of a mammal (e.g., a human) such as the gastrointestinal tract, blood vessels, tumors, lungs, kidneys etc. . . . One particularly useful form of imaging (e.g., visualization) is computed tomography (CT) imaging. Generally, the co-crystal or salt will be administered to the mammal by one of many routes of administration and the mammal will be imaged by an imaging technique such as CT imaging.
Contrast Agents.

Contrast agents are agents that are administered to a subject such as a mammal (e.g., a human) and allow for the visualization (e.g., computed tomography based on x-ray attenuation) of certain organs/tissues of the body of the subject such as blood vessels and tumors. One particular class of contrast agents are contrast agents that include one or more covalently bonded iodos (—I) which are termed iodinated contrast agents. These iodinated contrast agents are useful in computer tomography (CT) imaging as they attenuate X-ray radiation and thus allow for visualization. There exist many approved contrast agents including iodinated contrast agents for clinical use. One embodiment provides for clinically approved contrast agents (e.g., iodinated contrast agent) with the necessary chemical structure to associate with co-crystal formers. One embodiment provides for clinically approved iodinated contrast agent with one or more iodos and one or more hydrogen bond acceptors or hydrogen bond donors.

In one embodiment the contrast agent allows for the visualization of certain organs or tissues of the body of a subject upon administration.

In one embodiment the contrast agent is capable of attenuating X-ray radiation.

In one embodiment the contrast agent is used for computer tomography (CT) imaging.

In one embodiment the contrast agent is a molecule with a molecular mass of less than 1500 AMU.

In one embodiment the contrast agent is a molecule with a molecular mass of less than 1000 AMU.

In one embodiment the contrast agent is a molecule with a molecular mass of less than 750 AMU.

In one embodiment the contrast agent is an iodinated contrast agent.

In one embodiment the iodinated contrast agent includes one or more covalently bonded iodos wherein the iodinated contrast agent has a molecular mass of less than 1500 AMU.

In one embodiment the iodinated contrast agent includes one or more covalently bonded iodos wherein the iodinated contrast agent has a molecular mass of less than 1000 AMU.

In one embodiment the iodinated contrast agent includes one or more covalently bonded iodos wherein the iodinated contrast agent has a molecular mass of less than 750 AMU.

In one embodiment the iodinated contrast agent is a phenyl or pyrdin-4(1H)-one with one or more covalently bonded iodos wherein the iodinated contrast agent has a molecular mass of less than 1500 AMU.

In one embodiment the iodinated contrast agent is a phenyl or pyrdin-4(1H)-one with one or more covalently bonded iodos wherein the iodinated contrast agent has a molecular mass of less than 1000 AMU.

In one embodiment the iodinated contrast agent is a phenyl or pyrdin-4(1H)-one with one or more covalently bonded iodos wherein the iodinated contrast agent has a molecular mass of less than 750 AMU.

One embodiment provides an iodinated contrast agent comprising a molecule (e.g., a molecule with a molecular mass of less than 750 AMU or less than 500 AMU or less than 300 AMU) substituted with one or more iodos.

One embodiment provides an iodinated contrast agent comprising a a molecule (e.g., a molecule with a molecular mass of less than 750 AMU or less than 500 AMU or less than 300 AMU) substituted with one or more iodos and one or more H-bond donor groups or H-bond acceptor groups.

One embodiment provides an iodinated contrast agent comprising a a molecule (e.g., a molecule with a molecular mass of less than 750 AMU or less than 500 AMU or less than 300 AMU) substituted with one or more iodos and one or more H-bond donor groups.

One embodiment provides an iodinated contrast agent comprising a molecule (e.g., a molecule with a molecular mass of less than 750 AMU or less than 500 AMU or less than 300 AMU) substituted with one or more iodos and one or more carboxyl or hydroxy groups.

One embodiment provides an iodinated contrast agent comprising a molecule (e.g., a molecule with a molecular mass of less than 750 AMU or less than 500 AMU or less than 300 AMU) substituted with one or more iodos and one or groups selected from —$CO_2H$, —NHC(=O)$CH_3$, —N($CH_3$)C(=O)$CH_3$, —$CH_2$CH(OH)$CH_2$OH, —NH2 and —$CH_2$CH($CH_2$$CH_3$)$CO_2$H.

One embodiment provides an iodinated contrast agent comprising a phenyl or pyridin-4(1H)-one substituted with one or more iodos.

One embodiment provides an iodinated contrast agent comprising a phenyl or pyridin-4(1H)-one, wherein the phenyl or pyridin-4(1H)-one is substituted with one or more iodos and one or more hydrogen bond donor groups or hydrogen bond acceptor groups.

One embodiment provides an iodinated contrast agent comprising a phenyl or pyridin-4(1H)-one, wherein the phenyl or pyridin-4(1H)-one is substituted with one or more iodos and one or more carboxyl or hydroxy groups.

One embodiment provides an iodinated contrast agent comprising a phenyl or pyridin-4(1H)-one, wherein the phenyl or pyridin-4(1H)-one is substituted with one or more iodos and one or more groups selected from —$CO_2H$, —NHC(=O)$CH_3$, —N($CH_3$)C(=O)$CH_3$, —$CH_2$NHC(=O)$CH_3$, —$CH_2$CH(OH)$CH_2$OH, —$NH_2$ and —$CH_2$CH($CH_2$$CH_3$)$CO_2$H.

One embodiment provides an iodinated contrast agent comprising a phenyl, wherein the phenyl is substituted with one or more iodos and one or more groups selected from —$CO_2H$, —NHC(=O)$CH_3$, —N($CH_3$)C(=O)$CH_3$, —$CH_2$NHC(=O)$CH_3$, —$NH_2$ and —$CH_2$CH($CH_2$$CH_3$)$CO_2$H.

In one embodiment the iodinated contrast agent is diatrizoic acid (DTA), metrizoic acid, iodamide, iopydol, acetrizoic acid (ATA) or iopanoic acid (IPA):

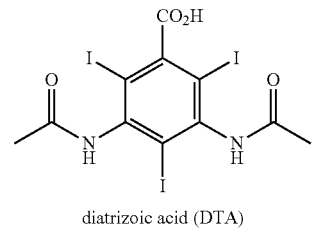

diatrizoic acid (DTA)

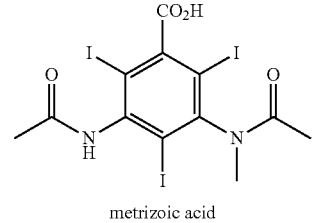

metrizoic acid

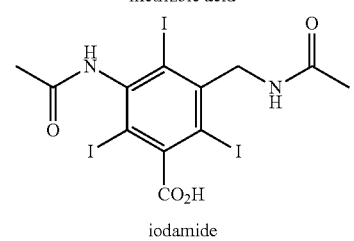

iodamide

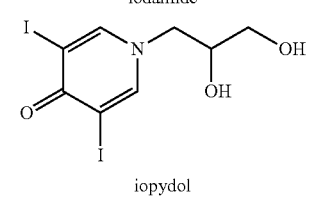

iopydol

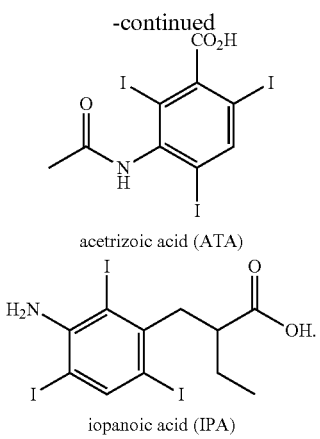

acetrizoic acid (ATA)

iopanoic acid (IPA)

In one embodiment the iodinated contrast agent is diatrizoic acid (DTA), metrizoic acid, iodamide, iopydol, acetrizoic acid (ATA) or iopanoic acid (IPA), or a salt thereof.

In one embodiment the iodinated contrast agent is diatrizoic acid (DTA), metrizoic acid, iodamide or iopydol.

In one embodiment the iodinated contrast agent is diatrizoic acid (DTA), metrizoic acid, iodoamide, acetrizoic acid (ATA) or iopanoic acid (IPA).

In one embodiment the iodinated contrast agent is diatrizoic acid (DTA), acetrizoic acid (ATA) or iopanoic acid (IPA).

In one embodiment the iodinated contrast agent is a compound of the following formula (iodixanol):

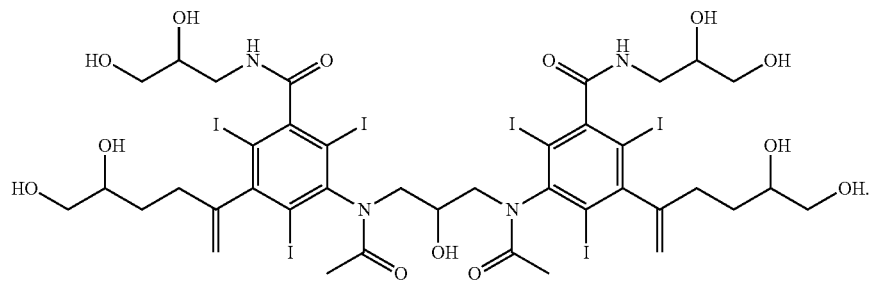 [SMILES: C=C(CCC(O)CO)c1c(I)c(C(=O)NCC(O)CO)c(I)c(N(CC(O)CN(C(C)=O)c2c(I)c(C(=C)CCC(O)CO)c(I)c(C(=O)NCC(O)CO)c2I)C(C)=O)c1I]

Co-Crystal Former

Co-crystal formers (CCFs) are components of the co-crystals and salts of the invention as described herein. The co-crystal formers can be any molecule (natural or man-made) that is capable of associating with the contrast agent to form a co-crystal or salt. For example, the CCF can associate with the contrast agent wherein no transfer of protons occurs between the contrast agent and the CCF and to form a co-crystal. The CCF can also associate with the contrast agent wherein transfer of one or more protons occurs between the contrast agent and the CCF (leading to a charged CCF and a charged contrast agent) to form a salt.

In one embodiment the co-crystal former associates with the contrast agent through non-covalent bonds.

In one embodiment the co-crystal former associates with the contrast agent through hydrogen bonds.

In one embodiment the co-crystal former associates with the contrast agent through ionic bonds.

In one embodiment the co-crystal former includes one or more hydrogen bond acceptor groups.

In one embodiment the co-crystal former is a molecule with a molecular mass of less than 1000 AMU.

In one embodiment the co-crystal former is a molecule with a molecular mass of less than 750 AMU.

In one embodiment the co-crystal former is a molecule with a molecular mass of less than 500 AMU.

In one embodiment the co-crystal former is a molecule with a molecular mass of less than 250 AMU.

In one embodiment the co-crystal former is a molecule with a molecular mass of about 50-750 AMU.

In one embodiment the co-crystal former is a molecule with a molecular mass of about 50-500 AMU.

In one embodiment the co-crystal former is a molecule with a molecular mass of about 50-250 AMU.

In one embodiment the co-crystal former includes one or more nitrogen atoms which are hydrogen bond acceptor groups.

In one embodiment the co-crystal former includes one or more N-aryl groups.

In one embodiment the co-crystal former has a molecular mass of less than 1000 AMU and includes one or more N-aryl groups.

In one embodiment the co-crystal former has a molecular mass of less than 750 AMU and includes one or more N-aryl groups.

In one embodiment the co-crystal former has a molecular mass of less than 500 AMU and includes one or more N-aryl groups.

In one embodiment the co-crystal former has a molecular mass of less than 250 AMU and includes one or more N-aryl groups.

In one embodiment the co-crystal former includes at least one pyridyl, phenazinyl or acridinyl.

In one embodiment the co-crystal former includes at least one pyridyl.

In one embodiment the co-crystal former is caffeine.

In one embodiment the co-crystal former is a natural molecule that includes at least one hydrogen bond acceptor (e.g., nitrogen).

In one embodiment the co-crystal former is pyridyl, phenazinyl, acridinyl or caffeine, wherein the pyridyl, phenazinyl or acridinyl are optionally substituted with one or more halo, —NH$_2$ or —(C$_2$-C$_8$)alkenylpyridyl.

In one embodiment the co-crystal former is pyridyl, phenazinyl, acridinyl or caffeine, wherein the pyridyl, phenazinyl or acridinyl are optionally substituted with one or more I, —NH$_2$ or —(C$_2$-C$_8$)alkenylpyridyl.

In one embodiment the co-crystal former is pyridyl, phenazinyl, acridinyl or caffeine, wherein the phenazinyl or acridinyl are optionally substituted with one or more I or —NH$_2$ and the pyridyl is optionally substituted with one or more or —(C$_2$-C$_6$)alkenylpyridyl.

In one embodiment the co-crystal former is pyridyl, phenazinyl or acridinyl, wherein the pyridyl, phenazinyl or acridinyl are optionally substituted with one or more halo, —NH$_2$ or —(C$_2$-C$_8$)alkenylpyridyl.

In one embodiment the co-crystal former is pyridyl, phenazinyl or acridinyl, wherein the pyridyl, phenazinyl or acridinyl are optionally substituted with one or more I, —NH$_2$ or —(C$_2$-C$_8$)alkenylpyridyl.

In one embodiment the co-crystal former is pyridyl, phenazinyl or acridinyl, wherein the phenazinyl or acridinyl are optionally substituted with one or more I or —NH$_2$ and the pyridyl is optionally substituted with one or more or —(C$_2$-C$_6$)alkenylpyridyl.

In one embodiment the co-crystal former is pyridyl, phenazinyl, acridinyl or caffeine wherein the phenazinyl or acridinyl is optionally substituted with one or more I or —NH$_2$ and the pyridyl is substituted with 2-(pyridin-4-yl)ethen-1-yl or 6-(pyridin-4-yl)hexa-1,3,5-trien-1-yl.

In one embodiment the co-crystal former is pyridyl, phenazinyl or acridinyl, wherein the phenazinyl or acridinyl is optionally substituted with one or more I or —NH$_2$ and the pyridyl is substituted with 2-(pyridin-4-yl)ethen-1-yl or 6-(pyridin-4-yl)hexa-1,3,5-trien-1-yl.

In one embodiment the co-crystal former is trans1,2-bis(4-pyridyl)ethylene (BPE), phenazine (PHE), acridine (ACR), trans, trans, trans-1,6-bis(4-pyridyl)-1,3,5-hexatriene (BPH or BHT), 3,6-diamino-4,5-diiodoacridine (DDA) or caffeine (CAF).

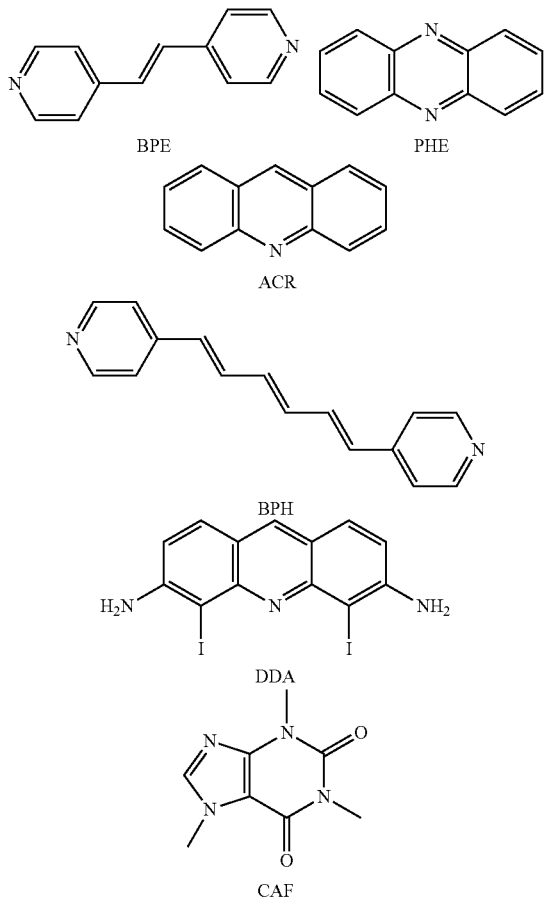

In one embodiment the co-crystal former is trans1,2-bis(4-pyridyl)ethylene (BPE), phenazine (PHE), acridine (ACR), trans, trans, trans-1,6-bis(4-pyridyl)-1,3,5-hexatriene (BPH or BHT), 3,6-diamino-4,5-diiodoacridine (DDA) or caffeine (CAF), or a salt thereof.

In one embodiment the co-crystal former is trans1,2-bis(4-pyridyl)ethylene (BPE), phenazine (PHE), acridine (ACR), trans, trans, trans-1,6-bis(4-pyridyl)-1,3,5-hexatriene (BPH or BHT) or 3,6-diamino-4,5-diiodoacridine (DDA).

In one embodiment the co-crystal former is trans1,2-bis(4-pyridyl)ethylene (BPE), phenazine (PHE) or trans, trans, trans-1,6-bis(4-pyridyl)-1,3,5-hexatriene (BPH or BHT).

Certain embodiments provide new contrast agents, e.g., nanoscale contrast agents (NCAs).

Certain embodiments provide a co-crystal that comprises a contrast agent and a co-crystal former (CCF).

In certain embodiments, the contrast agent is a computed tomography contrast agent.

In certain embodiments, the contrast agent is an iodinated contrast agent.

In certain embodiments, the contrast agent is diatrizoic acid (DTA), iodamide, metrizoic acid or iopydol.

In certain embodiments, the contrast agent is diatrizoic acid (DTA).

In certain embodiments, the CCF is 4,4'-bpe or caf.

In certain embodiments, the co-crystal is a nano-cocrystal.

In certain embodiments, the salt is a nano-salt.

In certain embodiments, the co-crystal is a nanosized-cocrystal.

In certain embodiments, the salt is a nanosized-salt.

Certain embodiments provide the use of the co-crystals described herein as imaging agents.

Certain embodiments provide the use of the co-crystals described herein as computed tomography imaging agents.

One embodiment provides a co-crystal or salt comprising:
a) an iodinated contrast agent; and
b) a co-crystal former.

One embodiment provides a co-crystal or salt comprising:
a) a contrast agent comprising one or more hydrogen bond donors or acceptors; and
b) a co-crystal former comprising one or more hydrogen bond donors or acceptors.

One embodiment provides a co-crystal or salt comprising:
a) a contrast agent comprising one or more hydrogen bond donors or acceptors; and
b) a co-crystal former comprising one or more hydrogen bond donors or acceptors, wherein the contrast agent and co-crystal former interact with each other by one or more hydrogen bonds.

One embodiment provides a co-crystal comprising:
a) a contrast agent comprising one or more hydrogen bond donors or acceptors; and
b) a co-crystal former comprising one or more hydrogen bond donors or acceptors, wherein the contrast agent and co-crystal former interact with each other by one or more hydrogen bonds wherein no transfer of protons has occurred between the contrast agent and the co-crystal former.

One embodiment provides a co-crystal comprising:
a) a contrast agent with a molecular mass of about 100-1000 AMU comprising one or more hydrogen bond donors or acceptors; and
b) a co-crystal former with a molecular mass of about 50-750 AMU comprising one or more hydrogen bond donors or acceptors, wherein the contrast agent and co-crystal former interact with each other by one or more hydrogen bonds wherein no transfer of protons has occurred between the contrast agent and the co-crystal former.

Halo as used herein includes fluoro, chloro, bromo, or iodo.

Carboxy and carboxylic acid refer to —$CO_2H$.

Alkenyl includes straight and branched all carbon chains containing one or more double bonds.

N-heteroaryl as used herein includes 6-membered monocyclic, 9-10 membered ortho-fused bicyclic and 12-14 membered ortho-fused tricyclic aromatic rings consisting of carbon and one to four heteroatoms each selected from the group consisting of non-peroxide oxygen, sulfur, and N(X) (wherein X is absent or is H, O, ($C_1$-$C_4$)alkyl) wherein at least one of the heteroatoms is N(X) wherein X is absent. Non-limiting examples of N-heteroaryls include pyridine, phenazine and acridine.

Pharmaceutical Formulations

The co-crystals and salts of the invention can be formulated as pharmaceutical compositions and administered to an animal (e.g., a mammal), such as a human patient in a variety of forms adapted to the chosen route of administration, i.e., orally or parenterally, by intravenous, intramuscular, topical, intrapulmonary, nasal or subcutaneous routes.

Thus, the co-crystals and salts of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral administration, the co-crystals and salts of the invention may be combined with one or more excipients and used in the form of ingestible tablets, buccal tablets, troches, capsules, elixirs, suspensions, syrups, wafers, and the like. The percentage of the compositions and preparations may, of course, be varied and may conveniently be between about 2 to about 60% of the weight of a given unit dosage form. The amount of active compound (e.g., contrast agent) in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the co-crystals and salts of the invention may be incorporated into sustained-release preparations and devices.

The co-crystals and salts of the invention may also be administered intravenously or intraperitoneally by infusion or injection. Solutions of the co-crystals and salts of the invention thereof can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The dosage forms of the co-crystals and salts of the invention suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the co-crystals and salts of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the co-crystals and salts of the invention may be applied in pure form, however, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the co-crystals and salts of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the co-crystals and salts of the invention to the skin are known to the art; for example, see Jacquet et al. (U.S. Pat. No. 4,608,392), Geria (U.S. Pat. No.

4,992,478), Smith et al. (U.S. Pat. No. 4,559,157) and Wortzman (U.S. Pat. No. 4,820,508).

Formulations suitable for intrapulmonary or nasal administration are administered by inhalation through the nasal passage or by inhalation through the mouth. Suitable formulations include aqueous or oily solutions of the co-crystals and salts of the invention. Formulations suitable for aerosol or dry powder administration may be prepared according to conventional methods.

Useful dosages of the co-crystals and salts of the invention can be determined by comparing their in vitro and in vivo properties. The amount of the co-crystals and salts of the invention required for use in will vary not only with the route of administration and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

Certain embodiments of the invention will now be illustrated by the following non-limiting Examples illustrated herein below.

Example 1

Materials and Methods

Diatrizoic acid dihydrate (meets USP testing specifications), p-toluenesulfonic acid monohydrate (≥98%), dichloromethane (≥99.8%), and methanol (ACS Reagent, ≥99.8%) were purchased from Sigma-Aldrich. Acridine (98%), phenazine (98%), chloramine-T trihydrate (≥97%), and potassium iodide (>99%) were purchased from Acros Organics. Iopanoic acid (>98%) was purchased from TCI America. Acetrizoic acid (>98%) and Proflavine HCl (>97%) were purchased from MP Biomedicals. Acetonitrile (99.9%), dimethylsulfoxide (≥99.9%), N,N-dimethylformamide (≥99.8%), magnesium sulfate (powder certified), sodium thiosulfate (≥98%), sodium bicarbonate (99.7%), and ethyl acetate (≥99.5%) were purchased from Fisher Scientific. Ethanol (100%) was purchased from Decon Labs. The compound trans,trans,trans-1,6-bis(4-pyridyl)-1,3,5-hexatriene was previously prepared based on a literature procedure (McWhinnie, S. L., et al., Inrg. Chem., 1996, 35(3), 760-774). All purchased chemicals were used as received. The document (John R. G. Sander, Ph.D. dissertation, University of Iowa, 2012) describes various procedures to prepare and characterize co-crystals and salts of the invention. This document is hereby incorporated by reference in its entirety.

Synthesis of 3,6-Diamino-4,5-diiodoacridine

DDA was synthesized based on a literature procedure (Martin, R. F., Aust. J. Chem., 1979, 32(12), 2637-2646). A round-bottom flask was charged with Proflavine HCl (1.4 g, 5.70 mmol) in water (150 mL). The solution was heated to 40° C. then solid $NaHCO_3$ was added until a pH of 10 was achieved. The suspension was filtered and a yellow solid was isolated. A round-bottom flask was charged with the yellow solid (1.0 g, 4.79 mmol), potassium iodide (1.982 g, 11.946 mmol), Chloramine-T (3.366 g, 11.946 mmol), and dimethylformamide (20 mL) then reacted at ambient conditions for 1 hour. The resulting suspension was poured into water and the product was extracted with 3×50 mL of ethyl acetate. The ethyl acetate fractions were combined, reacted with sodium thiosulfate (25 mg), dried over anhydrous $MgSO_4$, and evaporated using a rotary evaporator. To remove the p-toluene sulfonamide impurity, the resulting solid was dissolved in 250 mL of dichloromethane and excess ptoluenesulfonic acid monohydrate (1.26 g, 7.34 mmol) was added. After one hour of equilibration a dark red solid was isolated (608 mg 28% yield). $^1H$ NMR spectroscopy verified the spectrum of the isolated solid matched the previously reported spectrum for DDA.

Single Crystal Preparation

Single crystals of composition (DTA).2($H_2O$)(DTA1) were grown by slow-solvent evaporation. DTA (20 mg) was dissolved in a 1:1 (v/v) water ethanol solution and allowed to equilibrate to ambient conditions until single crystals were obtained. Single crystals of composition 2(DTA)$^-$.(2H-BPE)$^{2+}$.8($H_2O$) (DTA2) and (DTA).(PHE) (DTA3) were prepared via slow solvent evaporation. DTA2 and DTA3 were prepared from a 2:1 molar ratio (70 mg total) of DTA to CCF. Single crystals of DTA2 and DTA3 were obtained by dissolving the solid mixtures in a 1:1 (v/v) water ethanol or 1:1 (v/v) methanol acetonitrile solution, respectively. The solutions were left to slowly evaporate at ambient conditions until suitable single crystals were observed. Single crystals of composition (DTA)$^-$.(H-DDA)$^+$.4($H_2O$) (DTA4) were grown from the dissolution of a 1:1 molar ratio (27 mg total) of the cocrystal components in a 1:1:1 (v/v) ethanol water N,N-dimethylformamide solvent mixture. The solution was left to slowly evaporate at ambient condition until suitable crystals were observed.

Single crystals of composition 2(ATA)$^-$.(2H-BPE)$^{2+}$.1.2 ($H_2O$) (ATA1) and (ATA).(PHE)(ATA2) were achieved via slow-solvent evaporation of a 1:2 molar ratio (129 mg total) of ATA to CCF. ATA1 and ATA2 were obtained by dissolving the polycrystalline solids using a 1:1 (v/v) methanol acetonitrile solvent mixture. The solutions were allowed to equilibrate to ambient conditions and left undisturbed to slowly evaporate until single crystals were observed. Single crystals of (ATA)$^-$.(H-ACR)$^+$(ATA3) and (ATA)$^-$.(H-DDA)$^+$.2 ($H_2O$) (ATA4) were achieved via slow-solvent evaporation. A physical mixture of the cocrystal components in a 1:1 molar ratio (37 mg and 25 mg total) was dissolved in 1:1 (v/v) methanol acetonitrile or 1:1 (v/v) water ethanol respectively. The solutions were equilibrated to ambient conditions then solvent was allowed to slowly evaporate until single crystals were obtained.

Single crystals of compositions (IPA).0.5(BPE)(IPA1), (IPA).0.5(PHE) (IPA2), and (IPA).0.5(BPH)(IPA3) were prepared by dissolving a physical mixture of the cocrystal components present in a 2:1 ratio of IPA to CCF (132 mg, 132 mg, and 25 mg total respectively) in acetonitrile. After equilibration to ambient conditions the solvent was allowed to slowly evaporate until single crystals were observed.

Single Crystal X-Ray Diffraction Measurements

Crystal data was collected on a Nonius Kappa CCD single-crystal X-ray diffractometer at liquid nitrogen temperatures using graphite-monochromated MoKα radiation (λ=0.71073 Å). Structure solution and refinement was accomplished using SHELXL-97. All non-hydrogen atoms were refined anisotropically. Hydrogen atoms associated with carbon atoms were refined in geometrically constrained riding positions. If possible, hydrogen atoms associated with oxygen and nitrogen atoms were located in the Fourier-difference electron density maps.

ATA1 contains highly disordered solvent molecules. The Fourier-difference map revealed electron densities that could be ascribed to water molecules. Despite extensive use of restraints, an acceptable solvent model was not achieved. The crystal structure was treated with the SQUEEZE routine of PLATON. The solvent molecules were determined to occupy 45.0 Å$^3$. An electron count of 12 electrons per unit cell corresponds to approximately 1.2 molecules of water per asymmetric unit.

Results and Discussion

A series of structures based on iodinated contrast agents and CCFs that contain sp$^2$-hybridized N-atoms are reported herein. The $\Delta pK_a$ values between the carboxylic acid group of the contrast agents and the conjugate acid of the CCFs contributed to whether a co-crystal or a salt was obtained. Ten multi-component structures that contain iodinated contrast agents and CCFs were obtained. Five were co-crystals and five were salts.

Co-crystals based on iodinated contrast agents began with efforts to characterize DTA, ATA, and IPA via single crystal X-ray diffraction to understand behavior of these molecules in the solid-state. Efforts to grow suitable single crystals of ATA and IPA from a variety of solvents (i.e., polar to non-polar solvents that may or may not possess hydrogen bonding functionalities) resulted in needle-like crystals unsuitable for single-crystal X-ray diffraction. Alternatively, single crystals of DTA from a 1:1 (v/v) methanol water solvent mixture were obtained. Previous reports have characterized an anhydrous and a dihydrate form of DTA by infrared spectroscopy and X-ray powder diffraction yet, a full structural characterization of the molecule has not been found. Solid DTA1 crystallizes in the triclinic space group P1 with an asymmetric unit that comprises one DTA molecule and two water molecules. The DTA molecules assemble to give dimers that are arranged to form N—H (amide) . . . O(carboxy) (N . . . O: 2.829(4) Å) hydrogen bonds and weak I . . . π(3.86 Å) interactions. The remaining amide functionalities connect neighboring DTA dimers via N—H(amide) . . . O(carbonyl) (N . . . O: 2.831(5) Å) hydrogen bonds to extend the arrangement into a 1D column along the a-axis (FIG. 1).

The 1D columns stack along the c-axis via hydrogen bonding water molecules that assemble to form a cyclic tetramer. Specifically, DTA molecules donate a hydrogen bond to the water tetramer in the form of a O—H (carboxy) . . . O(water) (O . . . O: 2.507(5) Å) hydrogen bond and accept hydrogen bonds from water molecules via OH(water) . . . O(carbonyl) (O . . . O: 2.697(5) Å, 2.788(4) Å) interactions. The water tetramer is completed by O—H (water) . . . O(water) (O . . . O: 2.716(5) Å, 2.731(5) Å) interactions. The water rings effectively bridge neighboring DTA molecules into 2D sheets that stack with adjacent layers in an overlapping fashion sustained by weak I . . . I (3.95 Å) interactions.

Figure 2:
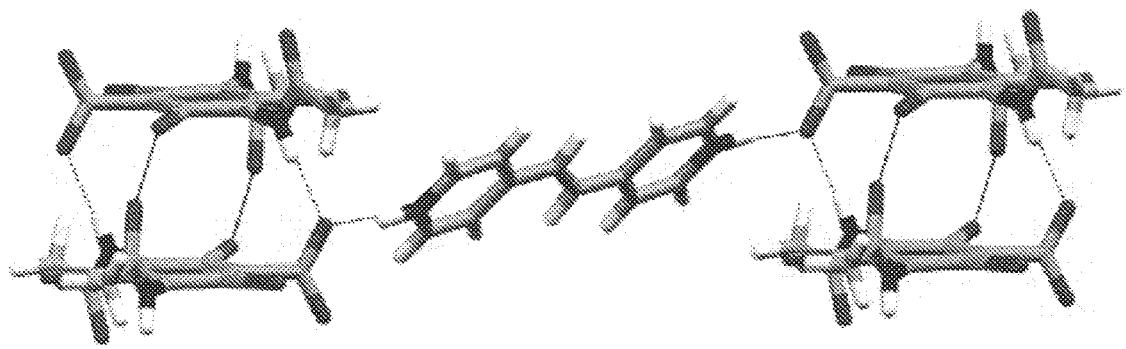
FIG. 2 shows the perspective of the X-ray crystal structure DTA2 wherein BPE molecules are oriented between DTA dimers (water molecules were omitted for clarity).

Co-crystallization studies were undertaken by employing CCFs that contain an aromatic N-atom capable of forming an O—H(carboxy) . . . N(pyridyl) heterosynthon. Specifically, the symmetric bipyridine BPE was selected, which is a simple bifunctional acceptor that forms co-crystals with a variety of hydrogen bond donors. Solid DTA2 crystallizes in the triclinic space group P1 with an asymmetric unit that contains two DTA, one half BPE that lies on a center of inversion, one half BPE that lies on a center of inversion and is unequally disordered over two orientations, and eight water molecules. The N-atoms of the BPE molecules are protonated by the carboxylic acid group of DTA. The DTA molecules of the salt are arranged to form charge assisted N$^+$—H(pyridinium) . . . O$^-$(carboxylate) (N . . . O: 2.505(5) Å, 2.558(6) Å) hydrogen bonds to the pyridinium rings of BPE (FIG. 2).

Akin to DTA1, the DTA molecules form dimers sustained by N—H(amide) . . . O(carbonyl) (N . . . O: 2.792(7) Å, 2.803(6) Å) hydrogen bonds and weak I . . . π(3.70 Å) interactions which hydrogen bond to BPE molecules to propagate a stepwise chain in the solid-state. The inclusion of water molecules results in two distinct acyclic chains that each comprises four water molecules. The water hydrogen bonding interactions result in a complex 3D network wherein the amide and carboxylate functionalities of DTA act as hydrogen-bond-donors and -acceptors to the water tetramers.

Figure 3:
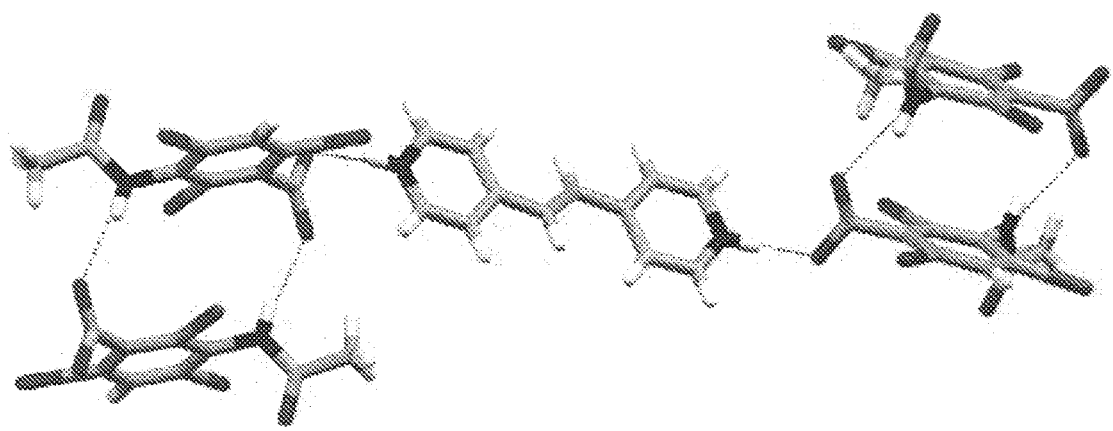
FIG. 3 shows the X-ray structure of ATA1 viewed along the b-axis (water molecules were omitted for clarity).

Owing to the salt formation and water affinity of DTA2 cocrystal formation between ATA and BPE was investigated. ATA offers a similar chemical composition to DTA but the benzoic acid derivative has a hydrogen atom at the 5 position instead of an amide group that may alter the water affinity. ATA and BPE crystallize in the triclinic space group P1 with an asymmetric unit that contains two ATA molecules and one BPE molecule. The N-atoms of BPE are protonated by the carboxylic acid group of ATA. Akin to DTA2, the protonated BPE molecules are arranged to form charge assisted N$^+$—H (pyridinium) . . . O$^-$(carboxylate) (N . . . O: 2.564(5) Å, 2.640(5) Å) hydrogen bonds with stacked ATA molecules (FIG. 3).

The stacked ATA molecules are sustained by N—H (amide) . . . O(carboxy) (N . . . O: 2.840(6) Å, 2.923 (6) Å) hydrogen bonds and weak I . . . π(3.98 Å) interactions. Akin to DTA2, the ATA and BPE molecular assembly extends in the solid-state to produce a stepwise chain. The 1D chains pack in an offset manner sustained by weak C—H . . . O forces and diffuse water molecules that fill the space between the voids to yield a 3D network. The water molecules present in the solid occupy approximately 2% of the unit cell contents.

Figure 4:
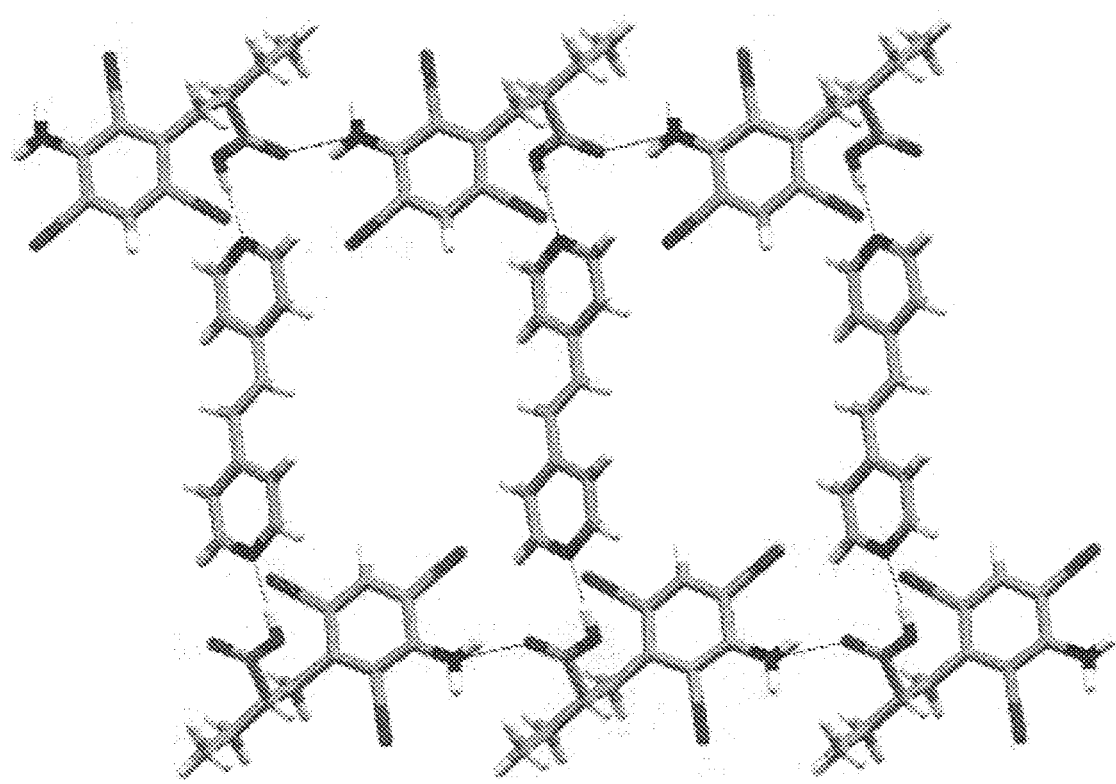
FIG. 4 shows the X-ray structure of IPA1 viewed along the c-axis to reveal a supramolecular ladder.
Figure 5:
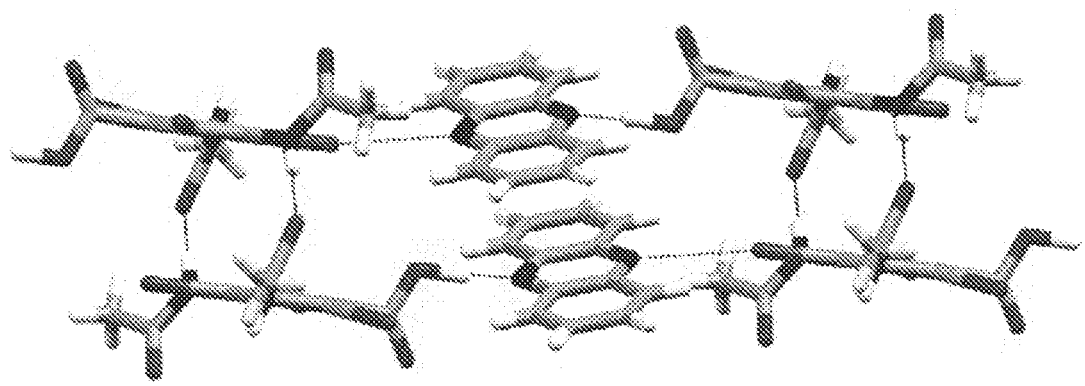
FIG. 5 shows the perspective view of DTA3 wherein PHE molecules hydrogen bond to a 1D column of DTA molecules.

The predominance of salt formation in DTA2 and ATA1 inspired co-crystallization studies with the contrast agent IPA. IPA retains a triiodobenzene core but, unlike the benzoic acid derivatives DTA and ATA, the carboxylic acid group of IPA is covalently bound to an aliphatic group. In this arrangement, IPA exhibits a reduced acidity (i.e., calculated $pK_a$ values are ~4.50 for IPA, ~0.92 for DTA, and ~1.13 for ATA; calculated values were obtained for the Sci-Finder Scholar database (2012) calculated using Advanced Chemistry Development (ACD/Labs) Software V11.02 (copyright 1994-2012 ACD/Labs)) that is expected to promote cocrystal formation with BPE. In fact, the components IPA and BPE crystallize in the absence of proton transfer in the space group P1 with one IPA molecule and one half BPE molecule that lies on a center of inversion. IPA and BPE assemble to form a carboxylic acid . . . pyridine heterosynthon (O . . . N: 2.712(5) Å) in an S-shaped arrangement. The assembly propagates in via N—H(amine) . . . O(carboxy) (N . . . O: 2.980(7) Å) hydrogen bonds along the a-axis to yield a supramolecular ladder (FIG. 4). The BPE molecules represent the rungs of the ladder with a separation distance of 9.57 Å. Adjacent supramolecular ladders pack in an interdigitated manner to fill the void between the rungs of the ladder that results in pronounced 2D layers. Neighboring layerspack in an overlapping fashion sustained by weak I . . . π(3.98 Å) interactions.

Based on a crystallization study with BPE it was determined that a CCF that contains an aromatic N-atom with a reduced basicity would promote cocrystallization with DTA, ATA, and IPA. Therefore, PHE owing to the availability of two aromatic N-atoms for the formation of supramolecular synthons and a lower $pK_a$ value than BPE (~1.60 versus ~5.50) was investigated.[3,4,9] The co-crystallization of DTA and PHE was investigated. The components of DTA3 crystallize in the triclinic space group P1 with an asymmetric unit that contains a DTA and a PHE molecule. The components formed O—H(carboxy) . . . N(pyridyl) (O . . . N, 2.647(5) Å) hydrogen bonds and weak I . . . N (3.12 Å) interactions between the DTA and PHE molecules Akin to DTA1-DTA2, the DTA molecules stack via N—H (amide) . . . O(carboxy) (N . . . O: 2.819(5) Å, 2.849(5) Å) to form a 1D chain along the a-axis. The PHE molecules stackalong the a-axis being separated by 3.85 Å and 5.73 Å. The pillared arrangement results in alternating columns of DTA and PHE to produce a 3D network. The neighboring layers of DTA3 stack in an ABAB manner than enables I . . . I (4.01 Å) interactions.

Figure 6A:
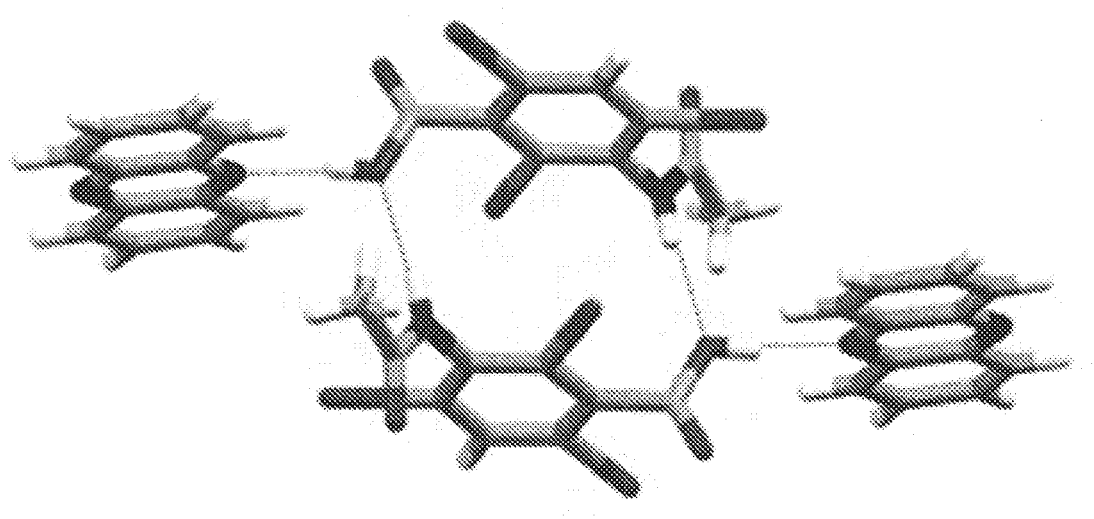
FIG. 6A shows the perspective view of the four-component assembly that comprises ATA2 and FIG. 6B shows the layers of ATA and PHE viewed along the a-axis.
Figure 6B:
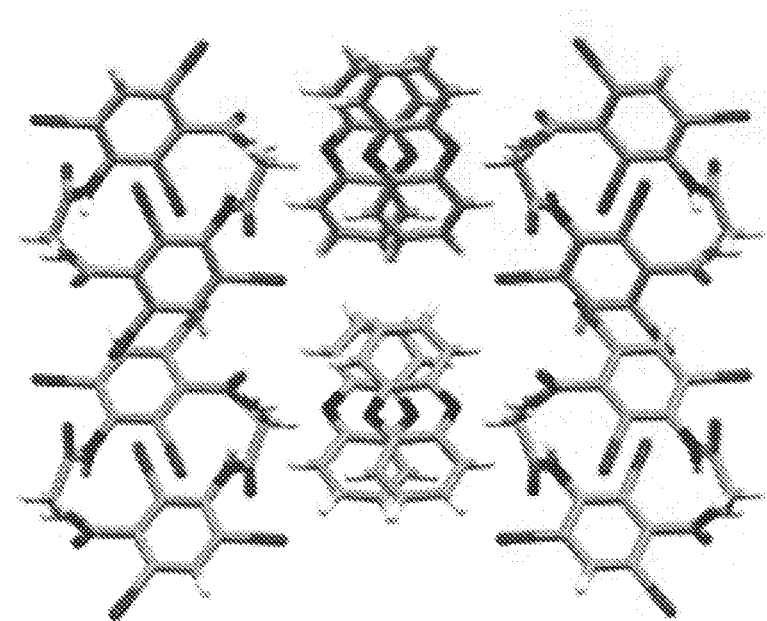

The ability of PHE to form co-crystals with iodinated contrast agents was further realized with ATA. The cocrystal components of ATA2 crystallize in the orthorhombic space group Pbca with a molecule of ATA and PHE in the asymmetric unit. The crystal structure is based on centrosymmetric four-component assemblies composed of two molecules of ATA and two molecules of PHE. The assembly is sustained by a dimer formation between ATA molecules, akin to ATA1, that contains N—H(amide) . . . O(carboxy) (N . . . O: 2.974(5) Å) hydrogen bonds and OH(carboxy) . . . N(pyridyl) (O . . . N, 2.624(5) Å) interactions between ATA and PHE to complete the assembly (FIG. 6A). The ATA dimers interact with adjacent dimers that have rotated to enable I . . . O (2.95 Å) interactions. The arrangement propagates into a layered structure along the b-axis. The PHE molecules stack in an offset manner to allow π . . . π interactions with a separation of 4.52 Å between the molecules. The extended 1D columns of PHE molecules pack in an interdigitated manner to enable C—H . . . π between the PHE molecules of neighboring columns. The resulting PHE columns are coupled with the ATA dimers to yield alternating layers of PHE and ATA (FIG. 6B).

Figure 7A:
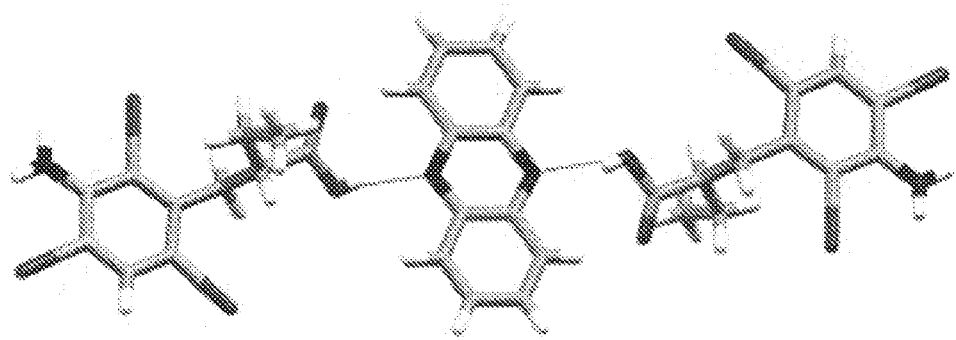
FIGS. 7A and 7B show the X-ray structure of IPA2.
Figure 7B:
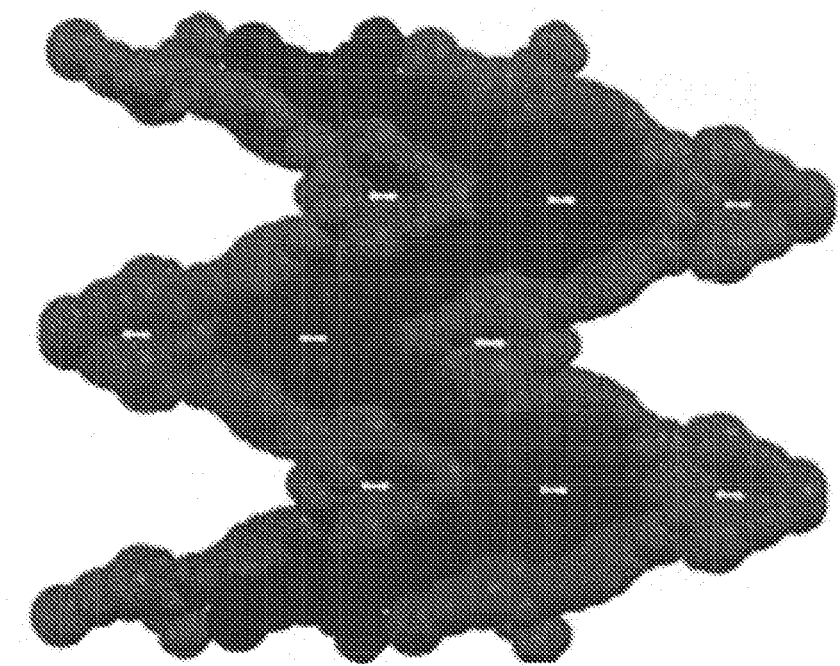

The third cocrystal with PHE involves IPA and PHE crystallizing in the monoclinic space group $P2_{1/c}$ with an asymmetric unit that comprises one IPA molecule and a half PHE molecule that lies on a center of inversion. The structure consists of a discrete three component assemblies involving two IPA molecules and one PHE that hydrogen bond via O—H(carboxy) . . . N(pyridyl) (O . . . N: 2.786(6) Å) interactions (FIG. 7A). Unlike IPA1, the aniline functionality of IPA does not participate in a hydrogen bond to extend the assembly into a supramolecular ladder. Consequently, the three-component assemblies form zig-zag chains via hydrophobic packing of the IPA alkyl chains. The chains interact in an offset manner via π . . . π interactions between IPA and PHE (FIG. 7B).

The role of the $\Delta pK_a$ between co-crystal components on cocrystallization was further investigated with the CCFs ACR, BHT, and DDA. Based on the calculated $\Delta pK_a$ values, crystallization of the CCFs with IPA would favor a co-crystal ($\Delta pK_a$<1.2) while crystallizations with DTA or ATA were expected to yield salts ($\Delta pK_a$>4.5).

Figure 8A:
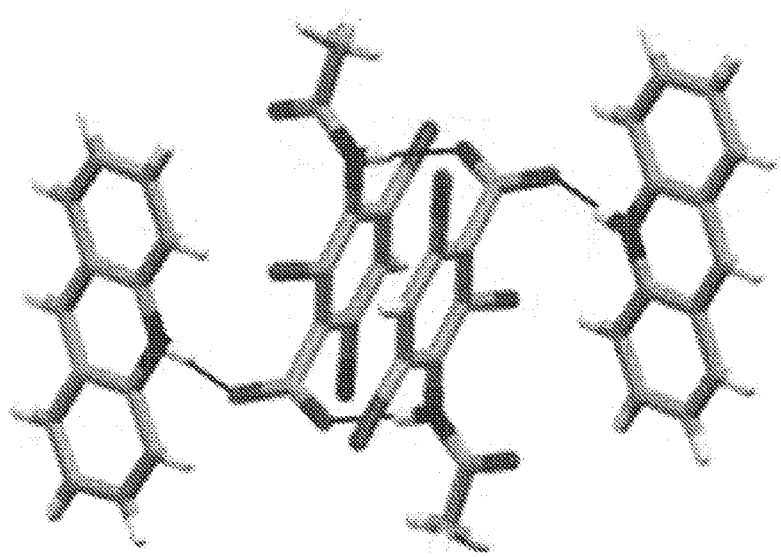
FIGS. 8A and 8B show the X-ray structure of ATA3.
Figure 8B:
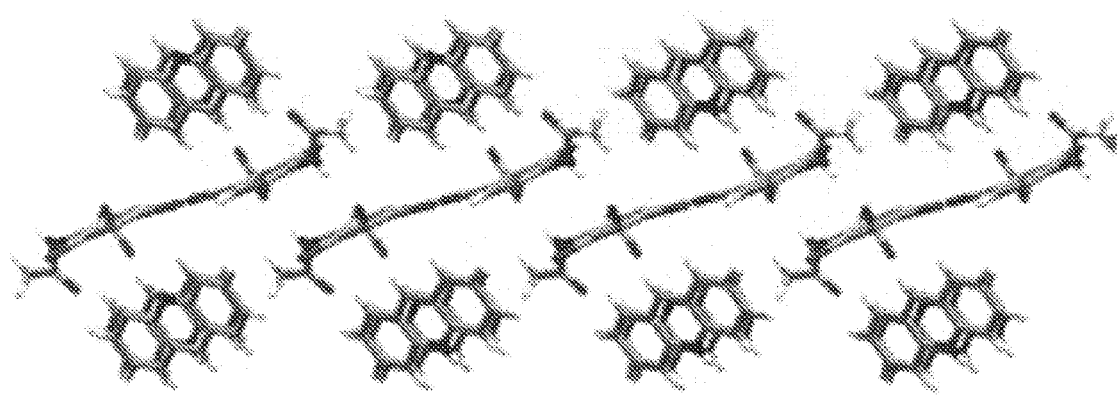

ACR contains a single aromatic N-atom of similar basicity to BPE. Thus cocrystal screening with ACR and the iodinated contrast agents is expected yield solids similar to the BPE trials with respect to salt or cocrystal formation. Cocrystallization trials with the contrast agents DTA, ATA, and IPA were conducted and single crystals of a multi-component solid composed of ATA and ACR (ATA3) were obtained. Solid ATA3 crystallizes in the triclinic space group P1 with a molecule of ATA and ACR in the asymmetric unit. The ATA molecules are arranged in a dimer motif similar to ATA1 and ATA2 wherein the amide functionalities participate in N—H(amide) . . . O(carboxy) (N . . . O: 2.815(3) Å) hydrogen bonds. The dimers arrange in a manner that enable I . . . O (2.83 Å) interactions between adjacent assemblies that propagates into a 1D chain. The packing of ATA chains is sustained by I . . . I (3.84 Å) interactions that extend the chains into a corrugated layer. The N-atom of ACR molecules is protonated by the carboxylic acid group of ATA molecules to form charge assisted $N^+$—H(pyridinium) . . . $O^-$(carboxylate) (N . . . O: 2.643 (4) Å) hydrogen bonds (FIG. 8A). The ACR molecules stack in an offset, head-to-tail, arrangement that consists of separation distances of 5.31 Å and 4.59 Å. The compilation of ATA and ACR columns results in a 3D arrangement based on alternating ATA and ACR layers (FIG. 8B).

Figure 9:
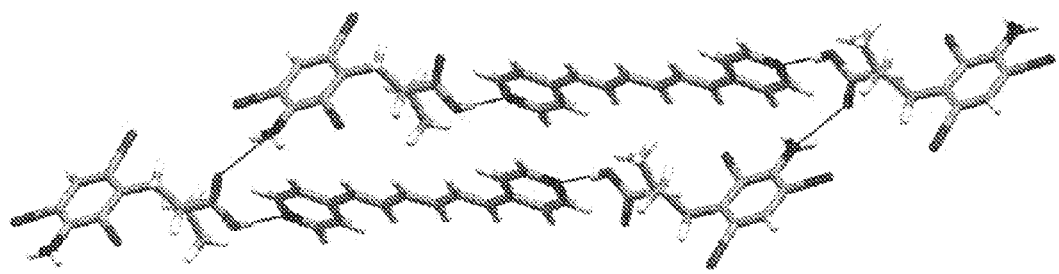
FIG. 9 shows the X-ray structure of IPA3 viewed along the a-axis to reveal a supramolecular ladder with BHT molecules serving as the rungs of the ladder.

Crystallization of IPA and BHT results in cocrystal formation. Solid IPA3 crystallizes in the triclinic space group P1 with an asymmetric unit that contains a molecule of IPA and a half molecule of BHT. IPA molecules are arranged to participate in OH(carboxy) . . . N(pyridine)(O . . . N: 2.709(7) Å) hydrogen bonds with each pyridyl ring of the BHT molecules. The IPA molecules extend this arrangement into a supramolecular ladder, similar to IPA1, through N—H (amine) . . . O(carboxy) (N . . . O: 2.923(7) Å) hydrogen bonds between neighboring IPA molecules. The BHT molecules serve as the rungs of the supramolecular ladder with separation distances of 10.46 Å (FIG. 9). The supramolecular ladders pack via I . . . I (3.70 Å) interactions between neighboring ladders to yield a 2D sheet. The layers of IPA3 stack in an offset manner sustained by weak C—H . . . N interactions between IPA and BHT molecules of adjacent layers and the hydrophobic packing of the alkyl chains of IPA within the void space between the rungs of the supramolecular ladders.

Figure 10:
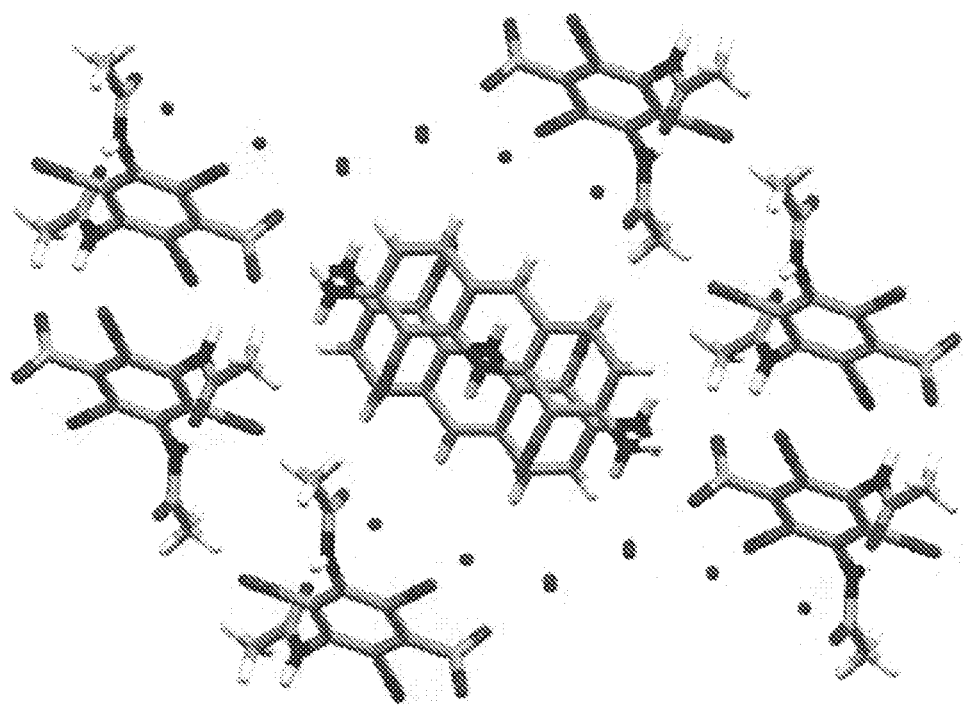
FIG. 10 shows the X-ray structure of DTA4 viewed along the a-axis, wherein, DTA and water molecules assemble into a channeled network that encapsulates stacked DDA molecules.

DDA possesses an aromatic N-atom and two iodine atoms that may sterically limit the accessibility of the N-atom. In addition, the calculated $pK_a$ of DDA (~5.74) suggests a high probability of salt formation with DTA and ATA. DTA4 crystallizes in the triclinic space group P1 with a DTA molecule, a DDA molecule, and four water molecules in the asymmetric unit. The aromatic N-atom of DDA molecules is protonated by the carboxylic acid group of DTA, which classifies this solid as a salt, not a cocrystal. Each DTA molecule of the salt is arranged to participate in N—H (amine) . . . O(carbonyl) (N . . . O: 2.800(8) Å) and NH(amine) . . . $O^-$(carboxylate) (N . . . O: 2.761(8) Å) hydrogen bonds with three neighboring DTA molecules which continues in a manner to which yields 1D columns based DTA molecules along the a-axis. The packing of DTA columns is sustained by I . . . O (3.30 Å) interactions and hydrogen bonding interaction with included water molecules. The water molecules assemble into a series of acyclic chains based on six water molecules that cross-link via hydrogen bonds to an additional two water molecules. The arrangement is similar to that of the classical description of a hairy polymer. The resulting hydrogen bonding interactions between DTA and water form a channeled structure wherein DDA molecules fill the void (FIG. 10). The DDA molecules within the columns stack in a head-to-tail arrangement separated by 3.49 Å and 4.72 Å. The carboxylate functionality of DTA molecules are anchor the DDA via N—H(amine) . . . O(carboxylate) (N . . . O: 3.093(10) Å) hydrogen bonds.

Figure 11:
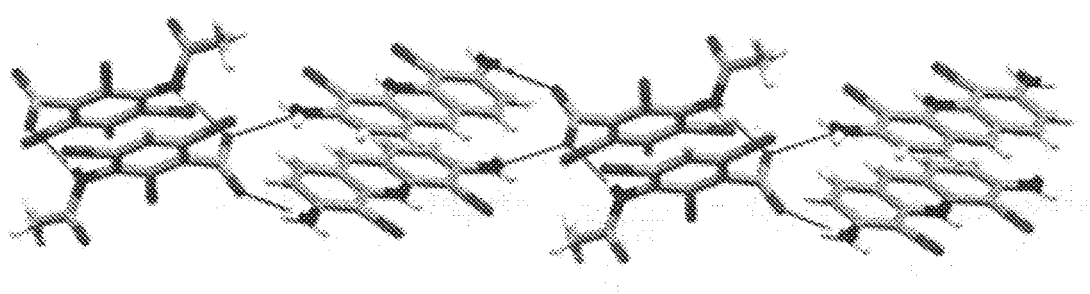
FIG. 11 shows the perspective view of the 1D chains that comprise ATA4 (water molecules have been omitted for clarity).

Similar to DTA4, crystallization of ATA and DDA results in protonation of the aromatic N-atom of DDA molecules by the carboxylic acid group of ATA molecules. ATA4 crystallizes in the triclinic space group P1 with an ATA molecule, a DDA molecule, and two water molecules in the asymmetric unit. As is the case in ATA1-ATA3, the ATA molecules arrange in a dimer motif sustained by NH(amide) . . . O(carbonyl) (N . . . O: 2809(5) Å). The carboxylate functionalities of the ATA dimers accept hydrogen bonds in the form of N—H(amine) . . . O(carboxylate) (N . . . O: 2.881(5) Å, 2.873(5) Å) interactions from DDA molecules. Between ATA dimers a pair of DDA molecules stacks in a head-to-tail fashion separated by 3.59 Å. The carboxylate-amine interactions extend to give 1D chains of alternating ATA and DDA dimers (FIG. 11). Owing to an additional carboxylate-amine interaction, adjacent chains pack in an ABAB manner within a 2D sheet. The layers of ATA4 participate in weak π . . . π and I . . . I interactions with crystallized water molecules completing the 3D packing. The water molecules are arranged as an infinite 1D chain that propagates along the a-axis Example 2. Preparation of Nano-Cocrystal Contrast Agents and Nano-Salt Contrast Agents Nano-cocrystal contrast agents as described herein were prepared by separately dissolving each component of the co-crystals (e.g., the contrast agent and the co-crystal former) in an appropriate solvent and then rapidly injecting the resulting solution(s) into an antisolvent to form a precipitate. Sonochemistry may be optionally utilized before, during, and after the precipitation. Nano-salt contrast agents can be prepared in a similar fashion. Methods to prepare nano-cocrystals are known and such methods may be used to prepare nano-cocrystals of co-crystals described herein (Bucar, D-K, et al., Journal of the American Chemical Society, 207, 129, 32-33; Sander, J. R. G., et al., Angew. Chem. Int. Ed., 2010, 49, 7284-7288). The contents of each of these documents is incorporated by reference in their entirety.

Example 3. Evaluation of the Co-Crystals and Salts of the Invention and Nanoscale Versions Thereof as Contrast Agents Contrast vs. molarity curves can be determined for the co-crystals and salts of the invention and will facilitate the selection of the molarity for in vivo animal studies that are expected to result in significant increases in image contrast. Co-crystals and salts of the invention with toxicity threshold molarities that are too low to enable significant contrast increases can be eliminated from further consideration.

The contrast versus molarity curves can be obtained using a modified 33 cm diameter Gammex (Middleton, Wis.) RMI 467 contrast phantom. The phantom contains inserts that represent tissues including bone, liver, breast, lung, fat, muscle, and brain, which can be used as references for determining the equivalent tissue contrast of the co-crystals and salts of the invention. Vials of co-crystals and salts of the invention and commercially available contrast agents with molarities ranging from 0 to 0.5 mol/l can be placed in customized acrylic inserts, inserted in the phantom, and CT-imaged. The contrast-to-noise ratio (CNR) can be used as a metric for quantifying contrast enhancement, as CNR is trivial to calculate.

Multiple CT systems can be used to assess the effectiveness of the co-crystals and salts of the invention for a variety of clinical situations. The effectiveness of the co-crystals and salts of the invention at enhancing diagnostic-quality CT image contrast can be assessed by imaging the customized RMI 467 phantom with the Siemens Biograph 40 PET/CT at three clinically-used X-ray beam energies: 80, 120, and 140 kVp. It is expected that the CT images with the highest contrast enhancement will be the 80 kVp images, since the k-edge of iodine, which is the source of the contrast enhancement of iodine, is 33.2 keV.

Phantom images can also be acquired with Siemens MVision™ cone beam CT (CBCT) systems that are used for tumor localization in stereotactic body radiation therapy (SBRT). The recent clinical adoption of SBRT has enabled the treatment of liver and pancreas cancer in three or fewer 20 Gy treatment sessions, rather than around 20 1.8-2 Gy, treatment sessions (deKrafft, K. E., Angew. Chem. Int. Ed. Eng. 2009, 48, 9901-9904). Since errors in patient setup have a higher impact when fewer sessions are used, CBCT image guidance is frequently used to acquire a 3-D image of the target region for patient alignment in SBRT. Liver and pancreas tumors are straightforward to identify on contrast-enhanced diagnostic CT images, but are very difficult to locate on CBCT images in the absence of contrast enhancement. The use of tumor contrast agents during radiotherapy to improve CBCT image quality for tumor localization has been suggested previously (Benedict, S. H., Med. Phys., 2010, 37, 4078-4101. It is possible that the potentially increased tumor specificity of functionalized co-crystals and salts of the invention could make them a valuable image guidance tool for SBRT. The relationship between co-crystals and salts of the invention concentration and image contrast in CBCT images can be determined to assess the clinical feasibility of co-crystals and salts of the invention enhanced CBCT imaging.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A nano-cocrystal or nano-salt comprising:
   a) a contrast agent wherein the contrast agent is phenyl or pyridin-4(1H)-one, wherein the phenyl or pyridin-4(1H)-one is substituted with one or more iodos and one or more groups selected from —$CO_2H$, —NHC(═O)$CH_3$, —N($CH_3$)C(═O)$CH_3$, —$CH_2$NHC(═O)$CH_3$, —$CH_2$CH(OH)$CH_2$OH, —$NH_2$ and —$CH_2$CH($CH_2CH_3$)$CO_2H$; and
   b) a co-crystal former comprising one or more N-aryl groups.

2. The nano-cocrystal or nano-salt of claim 1, wherein the contrast agent is diatrizoic acid (DTA), metrizoic acid, iodamide, iopydol, acetrizoic acid (ATA) or iopanoic acid (WA).

3. The nano-cocrystal or nano-salt of claim 1, wherein the contrast agent is diatrizoic acid (DTA), acetrizoic acid (ATA) or iopanoic acid (IPA).

4. The nano-cocrystal or nano-salt of claim 1, wherein the co-crystal former has a molecular mass of less than 500 AMU.

5. The nano-cocrystal or nano-salt of claim 1, wherein the co-crystal former includes one or more groups selected from pyridyl, phenazinyl and acridinyl.

6. The nano-cocrystal or nano-salt of claim 1, wherein the co-crystal former is pyridyl, phenazinyl or acridinyl, wherein the pyridyl, phenazinyl or acridinyl are optionally substituted with one or more halo, —$NH_2$ or —($C_2$-$C_8$) alkenylpyridyl.

7. The nano-cocrystal or nano-salt of claim 1, wherein the co-crystal former is trans1,2-bis(4-pyridyl)ethylene (BPE), phenazine (PHE), acridine (ACR), trans, trans, trans-1,6-bis(4-pyridyl)-1,3,5-hexatriene (BPH or BHT), 3,6-diamino-4,5-diiodoacridine (DDA) or caffeine (CAF).

8. The nano-cocrystal or nano-salt of claim 1, wherein the co-crystal former is trans1,2-bis(4-pyridyl)ethylene (BPE), phenazine (PHE), acridine (ACR), trans, trans, trans-1,6-bis(4-pyridyl)-1,3,5-hexatriene (BPH or BHT) or 3,6-diamino-4,5-diiodoacridine (DDA).

9. A pharmaceutical composition comprising the nano-cocrystal or nano-salt of claim 1, and a pharmaceutically acceptable carrier.

10. A method to image a mammal comprising administering the nano-cocrystal or nano-salt of claim 1 to the mammal and imaging the mammal.

11. The method of claim 10 wherein imaging is computed tomography imaging.

12. A method for preparing a nano-cocrystal or nano-salt of claim 1 comprising contacting a contrast agent with a co-crystal former.

13. The nano-cocrystal or nano-salt of claim 1 comprising:
   a) iopanoic acid (IPA); and
   b) a co-crystal former comprising one or more N-aryl groups.

14. A co-crystal or salt comprising:
   a) a contrast agent wherein the contrast agent is phenyl or pyridin-4(1H)-one, wherein the phenyl or pyridin-4(1H)-one is substituted with one or more iodos and one or more groups selected from —$CO_2H$, —NHC(═O)$CH_3$, —N($CH_3$)C(═O)$CH_3$, —$CH_2$NHC(═O)$CH_3$, —$CH_2$CH(OH)$CH_2$OH, —$NH_2$ and —$CH_2$CH($CH_2CH_3$)$CO_2H$; and
   b) a co-crystal former selected from phenazine (PHE), acridine (ACR), trans, trans, trans-1,6-bis(4-pyridyl)-1,3,5-hexatriene (BPH or BHT) or 3,6-diamino-4,5-diiodoacridine (DDA).

15. A co-crystal or salt comprising:
   a) a contrast agent wherein the contrast agent is phenyl or pyridin-4(1H)-one, wherein the phenyl or pyridin-4(1H)-one is substituted with one or more iodos and one or more groups selected from —$CO_2H$, —NHC(═O)$CH_3$, —N($CH_3$)C(═O)$CH_3$, —$CH_2$NHC(═O)$CH_3$, —$CH_2$CH(OH)$CH_2$OH, —$NH_2$ and —$CH_2$CH($CH_2CH_3$)$CO_2H$; and
   b) a co-crystal former selected from acridine (ACR), trans, trans, trans-1,6-bis(4-pyridyl)-1,3,5-hexatriene (BPH or BHT) or 3,6-diamino-4,5-diiodoacridine (DDA).

* * * * *

UNITED STATES PATENT AND TRADEMARK OFFICE
CERTIFICATE OF CORRECTION

PATENT NO. : 9,669,115 B2  
APPLICATION NO. : 13/931603  
DATED : June 6, 2017  
INVENTOR(S) : Leonard R. MacGillivray Page 1 of 1

It is certified that error appears in the above-identified patent and that said Letters Patent is hereby corrected as shown below:

In the Claims

Column 21, Lines 14-15, Claim 2, please delete "iopanoic acid (WA)" and insert -- iopanoic acid (IPA) -- therefor.

Signed and Sealed this  
Fifteenth Day of May, 2018

Andrei Iancu  
*Director of the United States Patent and Trademark Office*